United States Patent [19]

Fabinski et al.

[11] Patent Number: 5,459,075
[45] Date of Patent: * Oct. 17, 1995

[54] APPARATUS FOR MEASURING THE TOTAL CONTENT OF ORGANIC CARBON AND NITROGEN IN WATER

[75] Inventors: Walter Fabinski, Kriftel; Bernd Hielscher, Bad Vilbel; Peter Schlau, Frankfurt am Main; Christian Wolff, Karben, all of Germany

[73] Assignee: Hartmann & Braun AG, Frankfurt am Main, Germany

[*] Notice: The portion of the term of this patent subsequent to Mar. 8, 2011 has been disclaimed.

[21] Appl. No.: 125,410

[22] Filed: Sep. 22, 1993

[30] Foreign Application Priority Data

Sep. 22, 1992 [DE] Germany ............... 42 31 620.0

[51] Int. Cl.$^6$ ................. G01N 33/00; G01N 21/00
[52] U.S. Cl. ............ 436/114; 436/146; 422/82.05; 422/145; 250/344
[58] Field of Search ................. 436/114, 146; 422/82.05, 145; 250/344

[56] References Cited

U.S. PATENT DOCUMENTS

| | | | |
|---|---|---|---|
| 3,880,587 | 4/1975 | Szakasitz et al. | 422/68 |
| 4,066,402 | 1/1978 | Komiyama et al. | 436/114 |
| 4,271,124 | 6/1981 | Spector | 422/68 |
| 4,496,840 | 1/1985 | Fabinski et al. | 250/343 |
| 4,682,091 | 7/1987 | Fabinski et al. | 250/345 |
| 5,055,688 | 10/1991 | Fabinski | 250/344 |
| 5,106,754 | 4/1992 | Stoele et al. | 436/146 |
| 5,132,094 | 7/1992 | Godec et al. | 422/68.1 |

Primary Examiner—Robert J. Warden
Assistant Examiner—N. Bhat
Attorney, Agent, or Firm—Cohen, Pontani, Lieberman, Pavane

[57] ABSTRACT

An apparatus for measuring the total content of organic carbon (TOC) and nitrogen (TN) in water. The TOC value is correctly determined as the sum of the liquid, dissolved, and solid substances of a specimen of the water. The apparatus includes a NDIR gas analyzer for simultaneously measuring the concentration of $CO_2$ and NO gas components with a phase separator, a thermal reactor, a condenser, and two amplifiers for the pneumatic signals of the receivers with an indicator for the measured TOC and TN concentrations. The specimen is split into a gaseous part and a liquid part in the phase separator. The gaseous part which essentially contains the inorganic fraction of carbon, the TIC fraction, in the form of $CO_2$ gas is cooled in a condenser until a substantial fraction of its water vapor content is separated in the condenser by condensation. The dried gaseous part is directed via the comparison vessels as comparison gas. The gaseous part exiting from the comparison vessels is returned to the liquid part of the specimen again in its entirety and oxidized together with the latter in a thermal reactor. The gas specimen which is formed in so doing is charged via the condenser with water vapor having the same temperature as the comparison gas and is fed to the measurement chambers of the vessels as measurement gas which contains the entire carbon dioxide fraction and the entire nitrogen oxide fraction of the gas specimen.

5 Claims, 1 Drawing Sheet

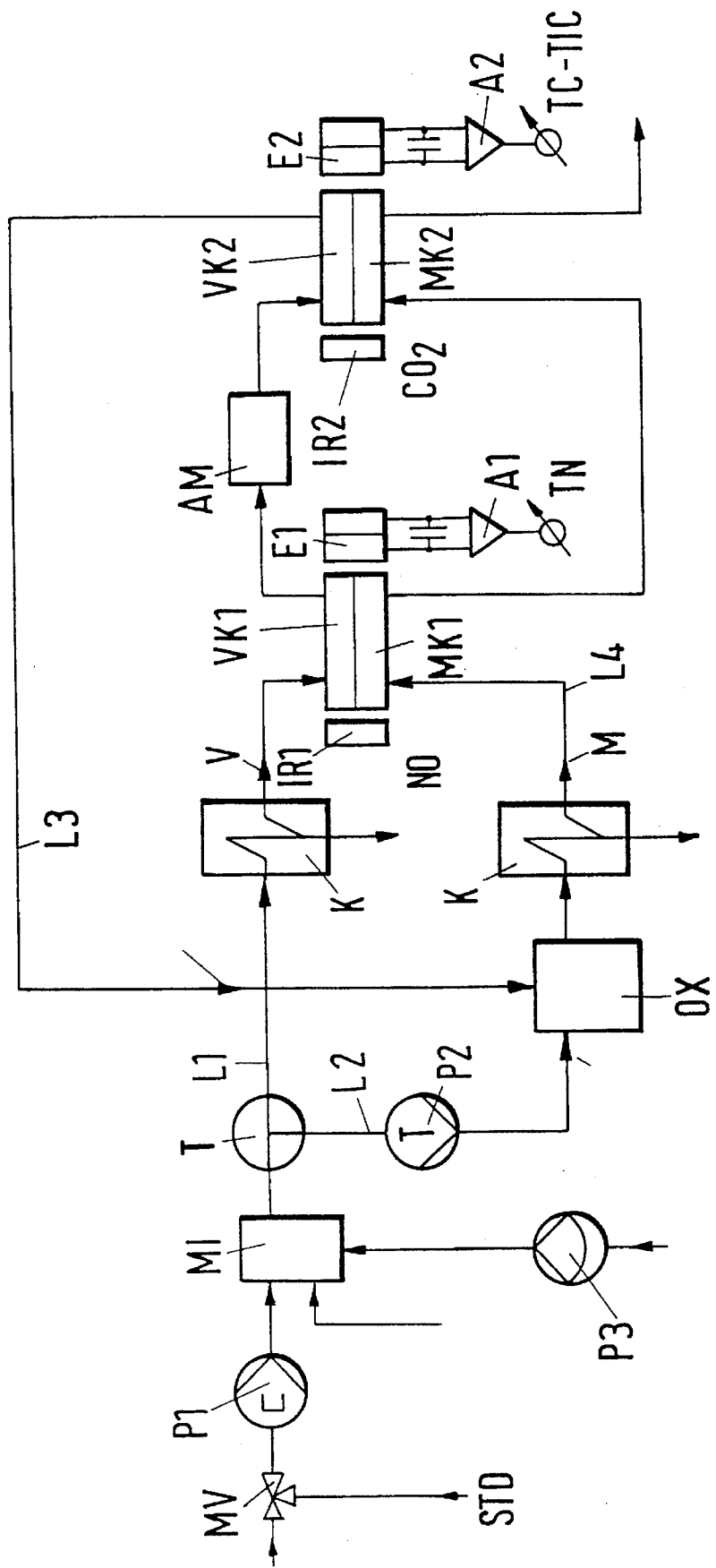

APPARATUS FOR MEASURING THE TOTAL CONTENT OF ORGANIC CARBON AND NITROGEN IN WATER

BACKGROUND OF THE INVENTION

1. Field of the Invention

The invention is directed to an apparatus for measuring the total content of organic carbon and nitrogen in water by evaporating a specimen taken from the water and oxidizing the organic carbon to form carbon dioxide and the nitrogen to form nitrogen oxide in a thermal reactor. The measurement is carried out on the basis of the gas specimen of carbon dioxide ($CO_2$) and nitrogen oxide (NO) formed from the specimen. A NDIR gas analyzer is used for the simultaneous measurement of the carbon dioxide and nitrogen oxide gas components, and has two adjacent vessels which are provided with the gas specimen and a comparison gas, respectively, and which are penetrated by modulated light beams from an infrared radiator. The light beams fall on pneumatic receivers arranged subsequent to the vessels after being partially absorbed in the vessels, and the receivers have two chambers arranged one after the other in the radiating direction, each of which is filled with one of the components of the gas specimen to be determined.

2. Description of the Prior Art

The abbreviations listed below are used throughout the application:

TOC (Total Organic Carbon) for the totality of carbon in the form of organic carbons present in the water to be measured;

TN (Total Nitrogen) for the totality of nitrogen present in the water to be measured;

TIC (Total Inorganic Carbon) for the totality of carbon in the form of inorganic compounds present in the water to be measured;

TC (Total Carbon) for the totality of carbon present in the water;

VOC (Volatile Organic Carbon) for the totality of carbon in the form of volatile organic compounds present in the water to be measured.

The organic fraction of carbon TOC is an oxygen-depleter and accordingly important for the analysis of water. The principle for determining the TOC amount is set forth in DIN 38409 (H) Part 3. Often, only a part, i.e. that of the dissolved TOC fraction, is detected in practice instead of the correct value. Volatile organic components which are lost when separating the specimen from inorganic components may also frequently be present in the water. Accordingly, the TOG value is not fully determined.

In addition to the TOC value, the fraction of bonded nitrogen TN is significant in that it allows assertions to be made concerning the loading of the water with nitrogen compounds from natural and industrial emitters. A suggestion for measurement is set forth in the DIN Draft 38 409 Part 27.

TOC analyses are known. TC and TIC are measured and calculated by subtracting TOC; (DE-OS 28 11 135, DE-OS 24 58 143, DE-AS 22 60 295, DE-OS 23 22 293, EP-PS 01 50 923). In isolated cases, an added TN measurement is included in a TOC measurement by providing a corresponding analyzer which is costly and creates undesirable delays in indication (DE-OS 26 21 616). Calibration is frequently effected manually with a high-purity null liquid for adjusting the zero value and with a test solution for sensitivity. Measurement errors based on the principle of measurement are also taken into account and thus there occur deviations from the given sensitivity when the base load of $CO_2$ changes.

SUMMARY OF THE INVENTION

Accordingly, it is an object of the present invention to provide an apparatus for the simultaneous measurement of the TOC content and TN content in water which detects both the dissolved and volatile components, takes into account zero shifts and changes in sensitivity based on changes in $CO_2$ when measuring TOC as well as cross-sensitivities relative to water vapor fractions in TN measurements and which enables a zero-point calibration without null liquid.

Pursuant to this object, and others which will become apparent hereafter, one aspect of the present invention resides in an apparatus in which a specimen of the water to be analyzed is split into a gaseous part and a liquid part in a phase separator. The gaseous part which essentially contains the inorganic fraction of carbon, the TIC proportion, in the form of $CO_2$ gas and partially also carbon fractions in the form of highly volatile hydrocarbon compounds is cooled in a condenser to approximately +8° C. until a predominant fraction of its water vapor content is separated in the cooler by condensation. The gaseous part which is dried in this way passes, as comparison gas, into a comparison vessel of a NDIR gas analyzer which operates by comparison of matter. This serves to compensate for the TIC fraction of the specimen and for the inevitable water vapor cross-sensitivity in the measurement of $CO_2$ and NO concentrations. The gaseous part exiting from the comparison vessel is returned in its entirety to the liquid part of the specimen and oxidized together with the latter in a thermal reactor. The oxidation of the specimen is effected for the volatile carbon fraction as well as for the carbon fraction dissolved in the water to form $CO_2$ and for the nitrogen fraction to form NO.

The gas specimen which is obtained in this way and which contains the entire carbon fraction and the entire nitrogen fraction of the specimen is separated from the water vapor in the condenser by condensation at the same temperature as the comparison gas and is guided to the measurement vessel of the NDIR gas analyzer as measurement gas. A pneumatic signal which corresponds to the concentration value of TC minus TIC and accordingly to the sought for TOC value occurs in a first receiver which is sensitized to $CO_2$. In a subsequent receiver, which is sensitized to nitrogen, a pneumatic signal occurs which corresponds to the difference of the nitrogen fraction of the measurement gas charged with water vapor and to the water vapor fraction of the comparison gas, i.e. to the sought for nitrogen fraction TN in the specimen.

The liquid pumps are switched off for the zero balance of the apparatus. $CO_2$ and NO are no longer formed in the thermal reactor. The air which continues to flow fills the measurement duct and comparison duct of the analyzer. This adjustment balances the $CO_2$ and NO offset changes of the system as well as the aging and impurities of the analyzer. The sensitivity of the TOC/TN measurement device is balanced by switching on the liquid pumps and by simultaneously switching a magnetic valve from measurement liquid to buffer liquid.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

The single figure is a block diagram of the invention.

DETAILED DESCRIPTION OF THE PREFERRED EMBODIMENTS

The inventive apparatus includes two liquid pumps P1 and P2 for pumping the specimen and a gas pump P3 for pumping the air for combustion. The valve MV makes it possible to switch to a standard liquid STD at the location of the specimen for adjusting the sensitivity of the entire arrangement. Acid, air and the specimen are mixed in the mixer MI. The mixture is moved to a phase separator T in which the liquid components are separated from the gaseous components.

The apparatus also has a thermal reactor OX, a condenser K, absorption means AM, and a known NDIR gas analyzer for simultaneously measuring the concentration of $CO_2$ and NO gas components.

The gas analyzer has two double-sided vessels with one half MK1, MK2 for the measurement gas M and one half VK1, VK2 for the comparison gas V. The vessels are irradiated by modulated light beams from two infrared radiators IR1 and IR2 which fall on pneumatic receivers E1 and E2 after partial absorption in the vessels. The receivers E1, E2 have two chambers which are arranged one after the other in the radiating direction and are filled with a component of the gas specimen to be determined. Receiver E1 is filled with the $CO_2$ component and receiver E2 is filled with the NO component.

A specimen of the water to be analyzed is pumped into the mixer MI by the pump P1. In so doing, acid and air are mixed in with the specimen. The inorganic carbon fraction TIC is converted into $CO_2$ gas in the mixer MI itself and along the path to the phase separator T and is fed to the condenser K via line L1. The predominant fraction of water vapor is removed from the $CO_2$ gas condensation at approximately 8° C. The $CO_2$ gas which is dried in this way reaches the comparison chamber of the vessels VK1 and VK2 as comparison gas V, flows through these vessels and arrives in the thermal reactor OX, where it is oxidized together with the liquid part of the specimen fed from the phase separator T via the line L2 to form $CO_2$ and NO. The gaseous oxidation product, the gas specimen, contains the total carbon fraction and nitrogen fraction of the aqueous specimen. The significant portion of the water vapor is extracted from the gas specimen in the condenser K by condensation at the same temperature of approximately 8° C. The dried gas specimen arrives in the measurement chamber of the vessels MK1 and MK2 of the gas analyzer as measurement gas M.

A pneumatic signal which corresponds to the concentration of the sought for nitrogen fraction TN occurs in the receiver E1. Since the comparison gas V contains $CO_2$, CO: absorption means AM are arranged prior to the comparison chamber VK2 of the $CO_2$ vessel and remove the inorganic COs from the comparison gas V. The measurement of TOC is not affected by the aging of the absorption means AM. Small transmitted amounts of inorganic $CO_2$ also arrive in the measurement chamber MK2 of the vessel.

A pneumatic signal corresponding to the difference of the organic $CO_2$ and the passed inorganic $CO_2$ minus the inorganic $CO_2$ occurs in the second receiver E2 which is sensitive to $CO_2$. This difference TC–TIC is indicated via the amplifier A2.

The cross-sensitivities relative to water vapor which occur in the measurement of NO can only be partially eliminated by condensation of the gases in the condenser K which is connected upstream. By directing the measurement gas M and the comparison gas V via the same condenser simultaneously and cooling them at the same temperature it is possible to adjust the measurement gas and comparison gas V to the same low water vapor content so that the cross-sensitivities occurring in the two vessels are compensated and the pneumatic signal in the receiver E2 corresponds to the correct value for the NO concentration in the gas specimen.

The zero point and the sensitivities of the measuring apparatus are subject to different influences which include aging and water vapor cross-sensitivities of the gas analyzer. To eliminate these influences, the measuring apparatus is balanced at given time intervals as follows:

The zero point is calibrated without null liquid. The pumps P1 and P2 are switched off. Air continues to be pumped only by pump P3. The air flows via line L1 along a cooling path of the condenser K into the comparison chambers VK1, VK2 of the vessels and via the thermal reactor OX into the measurement chambers MK1, MK2 of the vessels. $CO_2$ and NO are no longer formed in the thermal reactor OX. The pump P2 closes off the line L2 from the phase separator T to the reactor OX so as to be tight against gas and liquid. During this adjustment, the influences changing the zero point are balanced by electronic means in the amplifiers A1 and A2.

The sensitivity of the arrangement is calibrated by means of a calibrating liquid STI) which contains a known concentration of organic carbon and nitrogen. After the pumps P1 and P2 are switched on again and the magnet valve MV is switched to the calibrating liquid STD, the latter is fed to the apparatus. In addition to aging of the apparatus, impurities and aging of the pump P1, this adjustment also takes into account the aging of the $CO_2$ absorption means AM.

The receivers E1 and E2 deliver a pneumatic signal which corresponds to the known concentration of organic carbon and nitrogen compounds. The sensitivity of the amplifiers A1 and A2 which are connected downstream is adjusted with the signals generated in this way by electronic means. When the calibrating process is completed, the apparatus is reset again to the measurement operation for measuring the specimens removed from the water to be analyzed by reversing the valve MW.

The balancing process should be carried out every 2 to 28 days or at longer intervals depending on measurement conditions. For normal use, a 2-week balancing is sufficient when an accurate wobbling piston pump which remains constant over a long period is used for pump P2.

The volatile organic carbon compounds can be indicated separately by switching off only pump P2. The volatile organic compounds VOC are expelled from the specimen together with the inorganic carbon compounds TIC in the mixer MI. While the TIC fractions are converted with the acid to form COs and are absorbed in the $CO_2$ absorber AM, the VOC fractions arrive without hindrance in the thermal reactor OX and are there converted to $CO_2$. Since the switched off pump P2 does not deliver any liquid proportion of the specimen with TOC to the thermal reactor OX, only the VOC fraction is measured in this adjustment.

The invention is not limited by the embodiments described above which are presented as examples only but can be modified in various ways within the scope of protection defined by the appended patent claims.

We claim:

1. A method for measuring a total content of organic carbon and nitrogen in water, comprising the steps of:

for evaporating a specimen taken from the water and oxidizing the organic carbon to form carbon dioxide and the nitrogen to form nitrogen oxide, which together form a gas specimen of carbon dioxide and nitrogen oxide from which the measurement is carried out;

simultaneously measuring carbon dioxide and nitrogen oxide gas components in an NDIR, gas analyzer that includes two adjacent vessels with measurement and comparison chambers which are provided with the gas specimen and a comparison gas, respectively, and which can be penetrated by modulated light beams, an infrared radiator for providing the modulated light beams, and pneumatic receivers arranged subsequent to the vessels so that the light beams fall on the pneumatic receivers after being partially absorbed in the vessels, the receivers having two chambers arranged one after the other in a radiating direction of the light, each of the receivers being filled with one of the components of the gas specimen to be determined, a first one of the receivers being sensitized to carbon dioxide and a second one of the receivers being sensitized to nitrogen oxide, each of the receivers putting out pneumatic signals;

separating the gas specimen, which has an inorganic carbon dioxide fraction, and a liquid specimen fraction from the specimen;

loading the inorganic carbon dioxide fraction with water vapor so that the inorganic carbon dioxide fraction serves as the comparison gas;

feeding the comparison gas to the comparison chambers of the gas analyzer;

oxidizing carbon fractions and nitrogen fractions present in the specimen being oxidized;

charging the gas specimen with water vapor of the same temperature as the comparison gas;

feeding the gas specimen to the measurement chambers of the vessels as a measurement gas which contains the total carbon dioxide fraction and the total nitrogen oxide fraction of the gas specimen;

measuring a pneumatic signal from the first receiver which corresponds to a difference between a total carbon fraction and an inorganic carbon fraction and accordingly to an organic carbon fraction of the specimen;

and measuring a pneumatic signal from the second receiver which corresponds to a difference between a nitrogen oxide fraction of the measurement gas charged with water vapor and a water vapor fraction of the comparison gas and accordingly to a nitrogen oxide fraction of the specimen.

2. An apparatus for measuring a total content of organic carbon and nitrogen in water, comprising:

thermal reactor means for evaporating a specimen taken from the water and oxidizing the organic carbon to form carbon dioxide and the nitrogen to form nitrogen oxide, which together form a gas specimen of carbon dioxide and nitrogen oxide from which the measurement is carried out;

an NDIR gas analyzer for simultaneous measurement of carbon dioxide and nitrogen oxide gas components, the gas analyzer including two adjacent vessels with measurement and comparison chambers which are provided with the gas specimen and a comparison gas, respectively, and which can be penetrated by modulated light beams, an infrared radiator for providing the modulated light beams, and pneumatic receivers arranged subsequent to the vessels so that the light beams fall on the pneumatic receivers after being partially absorbed in the vessels, the receivers having two chambers arranged one after the other in a radiating direction of the light, each of the receivers being filled with one of the components of the gas specimen to be determined, a first one of the receivers being sensitized to carbon dioxide and a second one of the receivers being sensitized to nitrogen oxide, each of the receivers putting out pneumatic signals;

phase separator means for separating the gas specimen, which has an inorganic carbon dioxide fraction, and a liquid specimen fraction from the specimen;

condenser means for loading the inorganic carbon dioxide fraction with water vapor so that the inorganic carbon dioxide fraction serves as the comparison gas;

means for feeding the comparison gas to the comparison chambers of the gas analyzer, carbon fractions and nitrogen fractions present in the specimen being oxidized in the thermal reactor means, the gas specimen formed in the thermal reactor means being charged with water vapor of the same temperature as the comparison gas by the condenser means;

means for feeding the gas specimen to the measurement chambers of the vessels as a measurement gas which contains the total carbon dioxide fraction and the total nitrogen oxide fraction of the gas specimen;

first electric amplifier means for measuring a pneumatic signal from the first receiver which corresponds to a difference between a total carbon fraction and an inorganic carbon fraction and accordingly to an organic carbon fraction of the specimen;

and second electric amplifier means for measuring a pneumatic signal from the second receiver which corresponds to a difference between a nitrogen oxide fraction of the measurement gas charged with water vapor and a water vapor fraction of the comparison gas and accordingly to a nitrogen oxide fraction of the specimen.

3. An apparatus according to claim 2, wherein the means for feeding the measurement gas includes a first line arranged so as to guide the measurement gas from the condensor directly to a measurement chamber of the vessels, and further comprising a second line arranged so as to guide the comparison gas directly from a comparison chamber of the vessels to the thermal reactor means, a mixer for mixing the water specimen with air and acid, first pump means for pumping the specimen to the mixer, second pump means for pumping the liquid specimen fraction from the phase separator means to the thermal reactor means, the first and second pump means being switchable off so as to interrupt specimen flow during adjustment of a zero point of the gas analyzer.

4. An apparatus according to claim 3, and further comprising means for calibrating the apparatus using a calibrating liquid with contained substances for total organic carbon and total nitrogen as a specimen, the calibrating means including electric means for adjusting an adjustment of the zero point of the amplifiers, and third pump means for directing air via the mixer and the phase separator into the measurement chambers and comparison chambers of the vessels, the calibrating means calibrating sensitivity of the amplifier means after the pump means are switched on again and the calibrating liquid is introduced into the mixer.

5. An apparatus according to claim 3, wherein, for measuring volatile organic compounds in the water, the second pump means can be switched off so that no liquid specimen fraction reaches the thermal reactor from the phase separator.

* * * * *